(12) United States Patent
Emili (10) Patent No.: US 8,192,999 B2
(45) Date of Patent: Jun. 5, 2012

(54) METHOD FOR THE IDENTIFICATION OF MACROMOLECULE TARGETS OF ANALYTES

(76) Inventor: Andrew Emili, Toronto (CA)

( * ) Notice: Subject to any disclaimer, the term of this patent is extended or adjusted under 35 U.S.C. 154(b) by 377 days.

(21) Appl. No.: 11/813,331

(22) PCT Filed: Dec. 22, 2006

(86) PCT No.: PCT/CA2006/002112
§ 371 (c)(1),
(2), (4) Date: May 30, 2008

(87) PCT Pub. No.: WO2007/071060
PCT Pub. Date: Jun. 28, 2007

(65) Prior Publication Data
US 2008/0311610 A1 Dec. 18, 2008

Related U.S. Application Data

(60) Provisional application No. 60/752,918, filed on Dec. 23, 2005.

(51) Int. Cl.
*G01N 30/02* (2006.01)
*C07K 1/00* (2006.01)
(52) U.S. Cl. ........................................ 436/161; 530/417
(58) Field of Classification Search .......................... None
See application file for complete search history.

(56) References Cited

U.S. PATENT DOCUMENTS

| 5,891,742 | A | 4/1999 | Dollinger et al. |
| 6,656,690 | B2 | 12/2003 | Crooke et al. |
| 2003/0049647 | A1 | 3/2003 | Dahiyat et al. |
| 2006/0160131 | A1* | 7/2006 | Vandekerckhove et al. ... 435/7.1 |

FOREIGN PATENT DOCUMENTS

WO  WO 00/09654  2/2004

OTHER PUBLICATIONS

Von Rechenberg et al. Ampicillin/Penicillin-Binding Protein Interactions As a Model Drug-Target System to Optimize Affinity Pull-Down and Mass Spectrometric Strategies for Target and Pathway Identification; Proteomics, vol. 5 (2005) pp. 1764-1773.*
Zhen et al. Development of an LC-Maldi Method for the Analysis of Protein Complexes; Journal of the American Society for Mass Spectrometry, vol. 15 (2004) pp. 803-822.*
Baldwin, M.A. Protein Identification by Mass Spectrometry; Molecular and Cellular Proteomics 3.1 (2004) pp. 1-9.*
Salzano et al. Mass Spectrometry for Protein Identification and the Study of Post Translational Modifications; Ann. 1st Super Sanita, vol. 41, No. 4 (2005) pp. 443-450.*
Szpunar et al. Investigation of Metallodrug-Protein Interactions by Size-Exclusion Chromatography Coupled With Inductively Coupled Plasma Mass Spectrometry (ICP-MS); Analytica Chimica Acta, vol. 387 (1999)pp. 135-144.*
Muckenschnabel et al. Speedscreen: Label-Free Liquid Chromatography-Mass Spectrometry-Based High-Throughput Screening for the Discovery of Orphan Protein Ligands; Analytical Biochemistry, vol. 324 (2004) pp. 241-249.*
Allerdyce et al. Inductively Coupled Plasma Mass Spectrometry to Identify Protein Drug Targets From Whole Cell Systems; Chemical Communications (2001) pp. 2708-2709.*
Delahunty et al. Protein Identification Using 2D-LC-MS/MS; Methods, vol. 35 (Jan. 12, 2005) pp. 248-255.*
PCT International Search Report for PCT/US2006/002112.
Luesh, Hendrik "Towards high-throughput characterization of small molecule mechanisms of action." The Royal Society of Chemistry 2006, Molecular BioSystems, 2006, 2, 609-620.
Slon-Usakiewicz et al. "Frontal affinity Chromatography with MS detection (FAC-MS) in drug discovery." DDT, vol. 10, No. 6, Mar. 2005, 409-416.
Carr, S. et al. "The Need for Guidelines in Publication of Peptide and Protein Identification Data." Molecular & Cellular Proteomics, Jun. 2004;3(6):531-3. Epub Apr. 9, 2004.
Eng, J.K. et al. "An approach to correlate tandem mass spectral data of peptides with amino acid sequences in a protein database." Journal of the American Society for Mass Spectrometry. Volume 5, Issue 11, Nov. 1994, pp. 976-989.
Mann, M. & Wilm, M. "Error-tolerant identification of peptides in sequence databases by peptide sequence tags." Anal. Chem. 66,4390-4399 (1994).
Link, A.J. et al. "Direct analysis of protein complexes using mass spectrometry." Nat Biotechnol. Jul. 1999;17 (7):676-82.
Yates, J.R. III et al. "Peptide mass maps: a highly informative approach to protein identification." Anal Biochem. Nov. 1, 1993;214(2):397-408.
McCormack, A.L. et al. "Direct analysis and identification of proteins in mixtures by LC/MS/MS and database searching at the low-femtomole level." Anal Chem. Feb. 15, 1997;69(4):767-76.
Dongre, A.R. et al. "Emerging tandem-mass-spectrometry techniques for the rapid identification of proteins." Trends Biotechnol. Oct. 1997;15(10):418-25.
Mortz E. et al. "Sequence tag identification of intact proteins by matching tanden mass spectral data against sequence data bases." Proc Natl Acad Sci U S A., Aug. 6, 1996;93(16):8264-7.

* cited by examiner

*Primary Examiner* — Rebecca Prouty
*Assistant Examiner* — Paul Martin
(74) *Attorney, Agent, or Firm* — Bereskin & Parr LLP; Noel Courage (57) ABSTRACT

There is provided a method for the identification of macromolecule targets of analytes such as drugs in biological samples comprising complex mixtures of macromolecules. A biological sample is contacted with one or more analyte and the mixture is resolved such that the analyte and its target are co-eluted and analyzed to identify analyte-target complexes.

18 Claims, 11 Drawing Sheets

METHOD FOR THE IDENTIFICATION OF MACROMOLECULE TARGETS OF ANALYTES

FIELD OF THE INVENTION

This invention relates to the field of identification of analyte-biological macromolecule complexes. More specifically, the invention relates to the identification of the cellular protein(s) or other macromolecular targets of chemical compounds such as pharmaceutical compounds in the global context of complex biological mixtures, such as bodily fluids, tissue and cell extracts, and/or subcellular organelle fractions.

BACKGROUND OF THE INVENTION

Identification of biological targets, typically proteins, physically bound by chemicals such as pharmaceutical compounds is an important step in the design, optimization and clinical evaluation of bioactive therapeutic agents such as drugs and their metabolic byproducts as well as in the elucidation of their mechanisms of action.

Drugs typically function by binding to one or more cellular proteins (hereafter referred to as the target(s)), thereby perturbing the bound protein's function, either activating (as in an agonist) or inactivating (as in an antagonist) the protein's biological activity by altering the target's enzymatic activity, protein folding, or the protein's interactions with other molecules, etc. Optimally effective drugs usually display high binding affinity and specificity for the target(s), ideally selectively interacting with only a single protein family member, isoform or variant. In contrast, sub-optimal drugs often exhibit more promiscuity (i.e. less specificity in binding), leading to unwanted and/or unanticipated biological perturbations of multiple "off-target" cellular proteins or pathways leading to undesirable, biological effects and/or toxicity.

Modern therapeutic development is critically dependent on a process of systematic screening and optimization of the medicinal chemical properties of chemical compounds to meet stringent criteria defining the target specificity, affinity, and stability. Therapeutic prioritization is often based on critical insights gathered from careful elucidation of structure-function relationships and related biophysical properties, in particular target specificity and binding affinity, to assess lead agents and prioritize the selection of pharmaceutically active compounds for advanced clinical trials. Compounds exhibiting preferential target affinity and selectivity are usually preferred over less specific chemically distinct compounds.

The metabolism of lead compounds and drugs by cells and tissues can produce metabolite isoforms that exhibit either enhanced or reduced binding affinity and/or specificity for a given protein target, which can affect the compounds effectiveness, bioavailability, mode of action and/or stability. Knowledge of the preferential binding of one drug metabolite variant to a target protein(s) relative to other lead compounds can provide insight into optimal medicinal chemistry (e.g. drug structure-function relationships). Conversely, knowledge of the protein partners physically bound by various drug metabolites in affected cells and tissues can provide insights into their respective mechanisms of action, their relative effectiveness, and their target specificity.

Modern drug discovery usually occurs via either (i) a target-driven compound screening approach, wherein libraries of small synthetic chemical molecules or natural compounds are tested for specific binding to a particular protein of interest (aka the "target"), or (ii) via phenotypic screens, wherein a panel of compounds is screened for a desirable biological effect(s) upon treatment of healthy or diseased cells, tissues or model organisms, followed by the isolation and identification of the protein(s) targeted (i.e. bound) by the drug. The former approach typically involves the complete or partial elucidation of cellular pathways implicated in physiological functions that are altered in the disease state as a means of identifying biochemically desirable candidate macromolecules targets for therapeutic development (e.g. target profiling by functional screening). This approach often generates ineffective or toxic lead compounds in clinical trials since they frequently suffer from unexpected "off-target" effects due to unwanted non-selective binding to other non-targeted proteins. A major limitation of the latter approach is the lack of knowledge of the mechanism of action (e.g. the target(s)) of a lead compound. In both scenarios, identification of the protein(s) bound to be the lead compounds and its various in vivo metabolites in as near a physiological context as possible (that is, in the presence of all the available binding partner proteins present in an organelle, cell, or tissue) is crucial to confirming or elucidating the exact mode of drug action. Such information is essential for the development and validation of safe therapeutic agents with well-defined clinical indications.

The process of identifying drug targets and elucidating their downstream cellular effects occupies considerable effort in basic and pharmacological research. Classically, the identification of protein targets for phenotype-perturbing small molecules has been accomplished biochemically using labeled or immobilized molecules. Yet the identification of the physical targets of a drug has often proven to be exceedingly difficult firstly because introduction of a functional group (i.e. chemical derivitization) that may be used for immobilization or detection of the drug-target complex often changes the bioactive properties of the drug itself. Secondly, different drugs show a very wide range of affinities for their primary targets and to a greater or lesser degree to a range of secondary "off-target" proteins. In combination, these factors make it almost impossible to design and evaluate experiments aimed at identifying primary drug targets through direct physical capture on a generic level.

Identification of the protein(s) directly involved in cellular pathways has been greatly facilitated by the recent developments in proteomics, especially with the introduction of effective methods for the rapid separation, purification and mass spectrometry analysis (identification and quantification) of cellular proteins and protein complexes in tissue, cell and organelle extracts. Once potential targets have been biochemically isolated and identified, they are typically expressed in a heterologous host system and purified in recombinant form suitable for in vitro assays. Drugs can then be screened against these targets in vitro. Screening for compounds that can bind to known potential targets in isolation can be achieved by techniques that are well known in the art and may include, for example, frontal chromatography, tracking of labeled chemicals for their binding to immobilized potential targets using techniques such as fluorescence microscopy and binding assays in general. Conversely, drugs can be modified chemically to add a tether suitable for affinity isolation and then incubated with cell extracts with the hopes of enriching and purifying the target protein(s).

While examples of successful identification of drug targets have been reported in the literature, these methods are often prone to failure and typically require sizeable logistical efforts that make them unsuitable or impractical for rapid pre-screening of large-numbers of lead compounds. These aforementioned methods of drug screening also usually require the characterization of cellular pathways, which can be tedious and may often only resolve parts of a particular pathway or network of interacting, redundant pathways. Furthermore, the above-described approaches do not permit rapid identification of cellular targets in cases where compounds are massively screened for their effect on cells. For example, compounds for which the cellular target(s) is unknown may be found to be effective in achieving a desired effect such as inhibiting cell growth, but subsequent identification of the target may be very difficult or impossible with classical approaches. Also, while a particular compound may target proteins in a particular pathway, other proteins may also be bound by the compound, which may affect or alter its pharmacological properties and cellular effects. Ignorance of the identity of these other protein targets may impede the development of improved drugs.

As mentioned above, several biophysical methods have been developed to elucidate the direct binding targets of small molecules and drug-like compounds. These include Frontal-Affinity Chromatography (FAC), Nuclear Magnetic Resonance (NMR), Capillary Electrophoresis (CE). While these methods vary in their sensitivity, throughput and potential applications, they are universally non-optimal for identifying the proteins binding partners of lead compounds, drugs, and their metabolites in the context of complex biological mixtures, such as tissue homogenates, cell and organelle extracts, and biological fluids like blood or cerebral spinal fluid. In particular, a major unaddressed need is an easily implemented and readily generalizable method for accurately and rapidly discovering and sensitively monitoring those proteins that are selectively bound by a drug and its metabolites in the context of the myriad of proteins present in an organelle, cell, tissue, organ or entire organism.

There is therefore a pressing need for better (i.e. effective and generic) screening methods to identify and confirm the cellular protein targets of drugs and lead therapeutic compounds in complex protein lysates that have been prepared from cultured cells and/or tissues of model organisms or human blood specimens in a physiologically relevant manner. For maximal flexibility, the method should allow for the elucidation of drug targets using protein extracts prepared either before or after in vitro or in vivo treatment with a bioactive and control agents of interest.

SUMMARY OF THE INVENTION

In a broad aspect of the invention there is provided a method for identifying macromolecules targets of small molecules, lead therapeutic compounds and drugs and for monitoring the specificity of binding of drugs and their metabolites to macromolecules such as proteins in the context of complex biological mixtures consisting of hundreds to thousands of native (non-denatured) proteins and protein complexes present in cell secretions, solubilized membranes or soluble extracts prepared from isolated cells, subcellular organelles, tissues, organs, entire organisms, or other biological fluids.

An embodiment of the method provides for the screening of macromolecule (such as protein) lysates prepared from isolated cultured cells (e.g. primary, immortal, transformed or transfected cell lines) or animal or human tissues or cells of other model organisms after treatment with the compound(s) of interest prior to the preparation of protein extracts or following addition (spiking in) of a drug, related metabolites, or a set of compounds to a protein extract predicted or known to be enriched for a putative target protein prior to fractionation. The method allows for discovery, identification, monitoring and/or validation of the critical cellular protein target(s) of small molecules, drug or other lead therapeutic compounds or agents (including natural products, novel synthetic chemicals, and existing molecules) in various cell and tissue types for improving the development of novel, effective or specific medicinal treatments, for providing insights into mechanism of action or possible off-target effects (i.e. toxic, unexpected or otherwise undesirable secondary targets), as well as for developing suitable probes to investigate and perturb basic biological processes using chemical genomics approaches.

The method of the invention enables the tracking and identification of one or more targets in the context of clinically and physiologically relevant and realistic experimental setting in a global, biologically informative manner without the need for prior enrichment or knowledge and/or labeling of the protein target(s) or labeling of the agent(s) or small molecule(s) of interest. The method is generic, flexible, and readily adapted to various sources of targets (such as soluble or membrane-associated proteins isolated from different cell types, tissues, organisms, models, including partly purified protein mixtures, protein complexes, sub-cellular fractions, as well as biological samples containing other macromolecules such as nucleic acids, artificially "spiked" in recombinant peptides or proteins, and/or small molecules or chemicals as competitive agents) and the choice of therapeutic agent (including drugs, small molecules, lead compounds, compound libraries, peptides, or other molecules). The method is capable of high sensitivity and accuracy even when dealing with complicated biological samples, and provides both valuable qualitative (e.g. the identity of probable target(s)) and quantitative information (e.g. relative affinities) that can be used to understand the critical pharmacological properties of a drug-like molecule.

Thus, in one embodiment of the invention there is provided a method for identifying a macromolecule target of an analyte the method comprising: contacting the analyte with a sample comprising a plurality of macromolecules so as to allow binding of the analyte to one or more macromolecule target thereby generating at least one analyte-target complex; resolving the macromolecules including the at least one analyte-target complex based on one or more physico-chemical property of the macromolecules to produce macromolecule fractions, wherein biding of the analyte to the target is maintained during the resolving; and analyzing the macromolecule fractions to identify the one or more macromolecule target.

In another embodiment the method may further comprise a step of identifying macromolecule fractions comprising the analyte.

In another aspect, the method two or more separation protocols are used to resolve the macromolecules, each protocol exploiting a different physico-chemical property of the macromolecules, and wherein each fraction identified as comprising the analyte is analyzed to identify the one or more macromolecule target and wherein the identified macromolecule targets are compared to validate a macromolecule target identity.

In yet another aspect of the invention there is provided a method for establishing a diagnostic test, comprising identifying an analyte capable of generating a macromolecule binding profile that discriminates between a sample from a healthy individual and an individual known to have a disease.

In another embodiment there is also provided a method for diagnosing a disease with an analyte, comprising: generating a macromolecule binding profile for a sample from a healthy using the analyte to generate a control profile; generating a macromolecule binding profile for a sample from an individual in need of being tested for the disease using the analyte to generate a test profile; comparing the control and test profiles; and wherein differences between the test and the control profiles is indicative of presence of the disease in the individual.

Because neither the drug nor the target need be derivatized or modified in any way prior to either the cell or tissue treatment, protein separation or the subsequent detection by MS, the procedure is unlikely to create artefacts or perturb native drug-target interactions. The method is adaptable to any type of cell, tissue or drug, and has potential application in functional and mechanistic pharmacological studies, as well as the evaluation of chemical entities in terms of target specificity, toxicology and biological effect.

In the present description by macromolecule it is meant biological molecules such as proteins, protein complexes, lipids, glycolipids, carbohydrates, nucleic acids and the like.

By biological sample it is meant macromolecules solutions or suspensions, cells, cell extracts, bodily fluids, tissues and the like.

By analyte it is meant any small chemical molecule including but not limited to drugs, and their metabolites.

By resolving it is meant separating macromolecules based on physico-chemical properties to produce fractions comprising macromolecules such as to facilitate the subsequent analysis of the fractions to identify the one or more macromolecules present in any fraction. However, the separation is not necessarily intended to completely purify a macromolecule. In fact, in some embodiments of the invention, as will be further described below, it is desirable to resolve the macromolecules while preserving interactions that may exist between them. For example the separation may be design to prevent the disruption of complexes of proteins (proteasomes).

BRIEF DESCRIPTION OF THE DRAWINGS

Further features and advantages of the present invention will become apparent from the following detailed description, taken in combination with the appended drawings, in which.

DETAILED DESCRIPTION OF THE INVENTION

There is provided a method for identifying macromolecule targets of analytes such as pharmaceutical compounds. In accordance with an embodiment of the present invention the macromolecule target(s) of an analyte can be identified by contacting a compound of interest (the analyte) with a biological sample, resolving the macromolecules and analyzing the resulting fractions to identify the macromolecule target(s) of the analyte.

Figure 1:
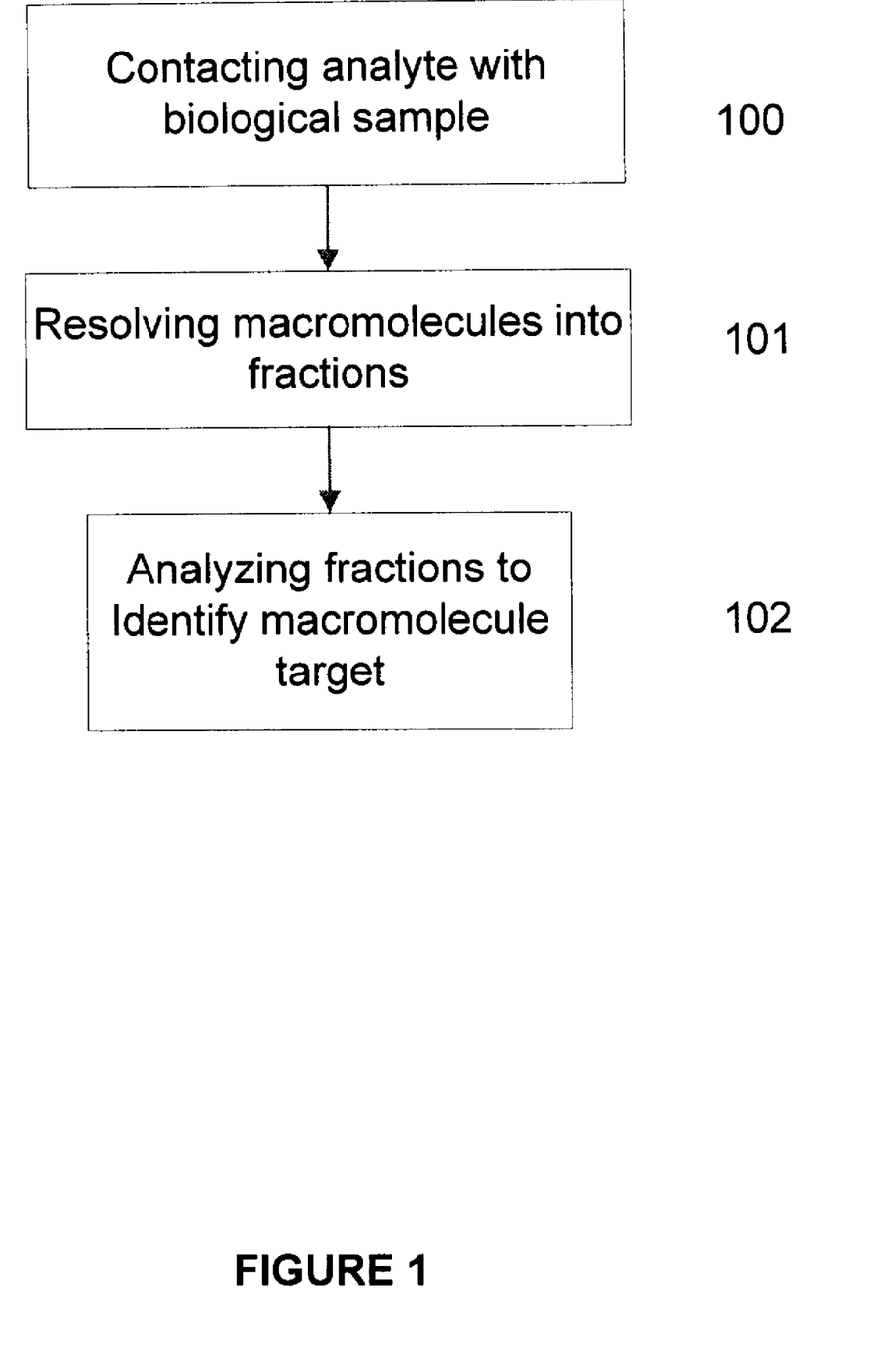
FIG. 1 is a flow chart diagram of an embodiment of the method of the invention.

A schematic diagram of the steps involved in an embodiment of the invention is shown in FIG. 1. The analyte (such as a drug for example) is contacted with a biological sample of interest at 100. The sample typically comprises a large number of macromolecules. The macromolecules are resolved at 101 to enable the subsequent identification of the macromolecules in the resulting fractions. The fractions are then analyzed at 102 to identify the macromolecule target(s) of the analyte.

Identification of the macromolecule target or analyte-macromolecule complexes can be achieved by various techniques such as western blotting, ELISA, biochemical assays and mass spectrometry. In a preferred embodiment identification is achieved by mass spectrometry. For example, liquid chromatography-mass spectrometry (LC-MS), nano-electrospray ionization tandem mass spectrometry (ESI-MS/MS), tandem mass spectrometry (MS/MS) and the like (see for examples Protein Sequencing and Identification Using Tandem Mass Spectrometry, M. Kinter and N. Sherman, John Wiley & Sons, D. Desiderio and M. Nibbering eds., 2000; The expanding role of Mass Spectrometry in Biotechnology, G. Siuzdak, MCC Press 2003 and U.S. Pat. No. 6,656,690 all references incorporated herein by reference). The resulting mass spectra can be screened against databases to identify the corresponding macromolecules. Macromolecules other than proteins can also possess affinity for the analyte and the invention is therefore not limited to proteins but extends to macromolecules such as lipids, carbohydrates and nucleic acids.

Direct analysis of proteins and protein complexes using LC-MS/MS after 1D and 2D-LC separations, can yield protein identification in a very short period of time. "Bottom up" shotgun profiling methods (such as collision induced dissociation and related ion fragmentation methods) leading to MS/MS fragmentation of the most intense precursor peptide ions in the MS spectra can yield amino acid sequence information that may be used to deduce the protein ID. "Top-down" whole protein characterization of intact proteins and their corresponding mass spectra can also reveal the presence of the chemical compound of interest on a particular protein or complex of proteins.

In a preferred embodiment the separation and identification of proteins (and parallel monitoring of the bound analyte or drug or metabolite) is performed using microcolumn LC or LC/LC in conjunction with automated (e.g. data-dependent, data-driven or data-directed) tandem mass spectrometry.

Protein separation at any given step is preferably conducted in the liquid phase in a buffer that is preferably compatible with the next (downstream) separation/identification step. Thus products of one separation step can be fed directly into the next liquid phase separation step therefore facilitating the automation of the process and providing for high throughput processing. It will be appreciated however that the sample may need to be processed to adjust the liquid phase parameters such as pH, ionic strength etc. between the different separation steps so as to adjust the condition to be compatible to the next step. Performing the separation in liquid phase also allows the pooling of fractions.

It will be appreciated that the binding of the analyte to a target such as a protein may be exploited in the separation and/or identification step. That is to say the binding of the chemical to the target may alter the physico-chemical properties of the chemical-target complex is such a way as to alter the behavior of the target in the separation and/or identification steps. For example the elution profile of the target may be altered providing information useful in the identification of the target.

Referring back to FIG. 1 the choice of macromolecule separation protocol and technique for resolving step 101 is dependent on the type of macromolecules to be analyzed. In one embodiment, the macromolecule targets are proteins and/or protein complexes which can be separated, after having been exposed to the analyte, by various fractionation techniques including but not limited to column chromatography (e.g. high performance liquid chromatography), capillary electrophoresis (CE), density gradient centrifugation or any such other analogous biophysical fractionation schema. Multi-dimensional separations techniques may also be used in which any particular dimension may employ any separation techniques including, but not limited to, size exclusion, ion exchange, normal/reversed phase partitioning, ion exclusion, ligand exchange, affinity portioning, capillary electrophoresis, liquid/gel phase isoelectric focusing, adsorption chromatography, selective retention, and the like. The protein fractions can be displayed in a 2-D map with each dimension corresponding to the separation based on one particular biophysico-chemical characteristic. As will be known to those skilled in the art, the map can be generated using specialized software.

The macromolecules resolving step does not necessarily implies the complete purification of any particular macromolecule. The purpose of macromolecules separation following incubation with the analyte is to provide macromolecule fractions amenable to the identification of the macromolecules and in particular of the macromolecule target(s). Thus the separation preferably does not affect the binding of analyte to target. Furthermore, the target(s) may consist of macromolecule complexes, such as proteasomes, and it is desirable to maintain these complexes intact during the separation process.

The identification of the targets may involve the combination of multiple separation and/or identification steps. For example, chromatographic separation may reveal multiple proteins or protein complexes co-eluting with the analyte. Refinement of the separation may be accomplished by modifying the conditions under which the chromatography is carried out. Also, the elution profile of some proteins may not necessarily perfectly coincide with that of the analyte-target complexes. In such instances further chromatography under different conditions may help in determining whether a protein is a target.

As mentioned above, the separation of the macromolecules enables the identification of macromolecule targets. In this respect, multiple separation steps can be performed to validate the identification of the target based on the fact that only a valid target is likely to co-purify with the analyte under different separation conditions, permitting the ready deconvolution of the correct analyte-macromolecule(s) pair(s).

Figure 2:
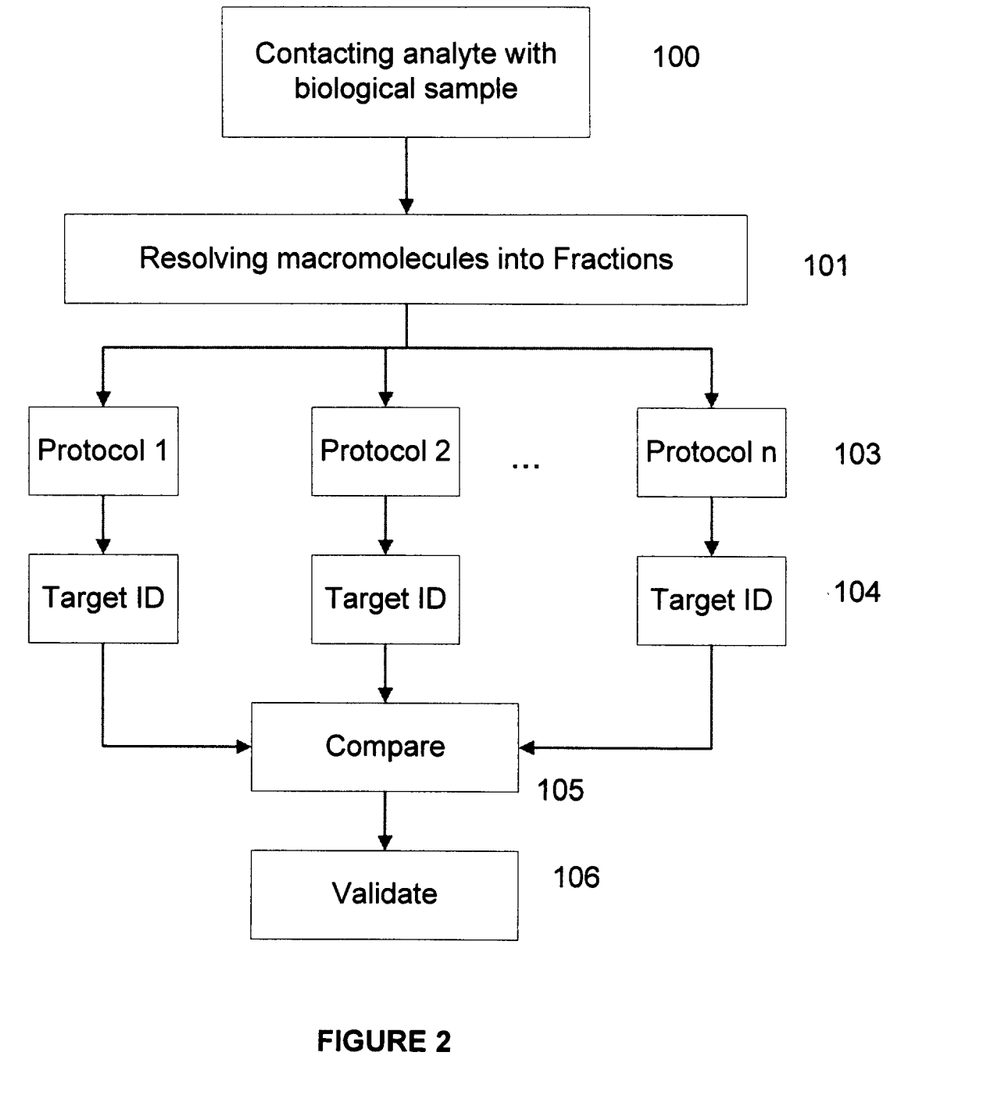
FIG. 2 is a flow chart diagram of another embodiment of the method of the invention showing multiple separation steps for validation of target identity.

Thus, referring to FIG. 2, the fractions obtained as a result of the multiple resolving steps 103 are analyzed at 104 to identify those fractions comprising the analyte and to determine the target(s) identity. The results of the analysis and identification can then be compared at 105 to validate the identity of the target or targets at 106.

The multi separation protocols approach also permits the rapid selection of macromolecule separation protocols that are compatible with the identification of targets for given type of biological samples and analytes.

That the correct fraction and hence macromolecule target has been identified can also be confirmed by dose-response analysis (increasing amount of the target protein leads to an increased retention of the drug relative to free compound). The interaction can also be confirmed by repeating the experiment using a sample derived from a cell bearing a mutated derivative of the target or depleted for the target.

The macromolecule fractions may be pre-screen for the presence of analyte such a to earmark these fractions for further analysis to identify the analyte target. Pre-screening for detection of the analyte may be achieved using techniques that are well known in the art such as spectroscopy (UV, Visible etc.) mass spectrometry, enzymatic assay and the like.

Alternatively the target(s) is identified by directly analyzing the fractions to simultaneously identify the target and the analyte bound thereto. This can be achieved for example by the separation and identification of proteins and parallel monitoring of the bound analyte or drug or metabolite using microcolumn LC or LC/LC in conjunction with automated (e.g. data-dependent, data-driven or data-directed) tandem mass spectrometry.

The mass spectrometry profile (fragmentation signature) of the analyte may be determined prior to contacting it with the sample. Knowledge of the analyte's profile facilitates the direct identification of analyte-macromolecule complexes.

The method of the invention may also be used to identify macromolecule targets of multiple analytes simultaneously thereby providing high throughput capabilities.

Since several macromolecules (proteins for example) can be present in any fraction, when dealing with a complex cell mixture or sub-cellular organelle, more than one target candidate can conceivably be present in a fraction. Hence, in a preferred embodiment, the high coverage and quantitative capabilities of mass spectrometry-based proteomic screening procedures are exploited to resolve the identity of the true target.

In an embodiment of the invention, proteasomes (protein complexes) can be identified as targets. Subsequent analysis of the target proteasome can reveal the composition of the proteasome in term of the individual proteins that are part of the complex.

The method of the present invention can also be used to establish a macromolecule profile of a cellular response to the presence of an analyte. Because the method of the invention also determines the presence of co-localized or interacting macromolecules and their relative abundance following treatment of the cell with a chemical entity or drug-like molecule, the global response of the cell to a compound is also revealed thereby providing a molecular pharmacological response profile. In yet another aspect of the invention it is also possible to exploit the current method to characterize the target profile of several chemical compounds or drugs simultaneously thereby enabling the molecular understanding of drugs compatibility.

The method of the invention described above can also be applied during the medicinal chemistry stage of drug development to help optimize drug-target interaction parameters, and to track the effects of metabolism on analyte protein binding and specificity. Moreover, in addition to revealing the identify of the protein(s) bound by a compound of interest, both the drug itself and the cellular response to it can also be characterized in terms of both protein sub-cellular re-localization and changes in relative abundance or even disruption or induction of interactions among proteins to form drug-dependent or drug-perturbed protein complexes.

The analyte may be contacted with any type of biological sample of interest. Thus the sample may consist of macromolecule solutions such as protein solutions, whole cells, such as mammalian cells, bacteria and viruses, cellular organelles, and organs or biological tissues. The sample may be derived from an organism or individual that has been exposed to an analyte (such as a drug). The organisms or individuals may include but are not limited to mammals such as humans or small animals (rats and mice for example) When the sample is not a macromolecule solution it will be appreciated that it is necessary to process the sample to extract macromolecules prior to separation and analysis to identify the target(s).

In another embodiment, there is provided a method for establishing a diagnostic test. The underlying cause of most disease is abnormal expression or activity of biochemical pathways and biological systems. Abnormal expression of macromolecules may, for example, results in an altered molecular structure which can affect the function of the molecule. The binding profile of an analyte can therefore be modified if its target is affected in disease state. Thus, the diagnostic test is established by screening analytes against samples from a diseased individual to identify an analyte exhibiting an altered target binding behavior when compared to target binding to macromolecules from a sample of a healthy individual.

The diagnostic test can be used to test individuals suspected of having a disease such as but not limited to cancer, neurodegenerative diseases, bacterial infections, viral infections, musculo-skeletal disorders and the likes.

The method may also be exploited to identify targets in diseased cells. For example, macromolecule profiling using the method of the invention can reveal differences between normal and diseased cells that can be exploited to identify targets for drug design and testing.

EXAMPLES

Example 1

Figure 3:
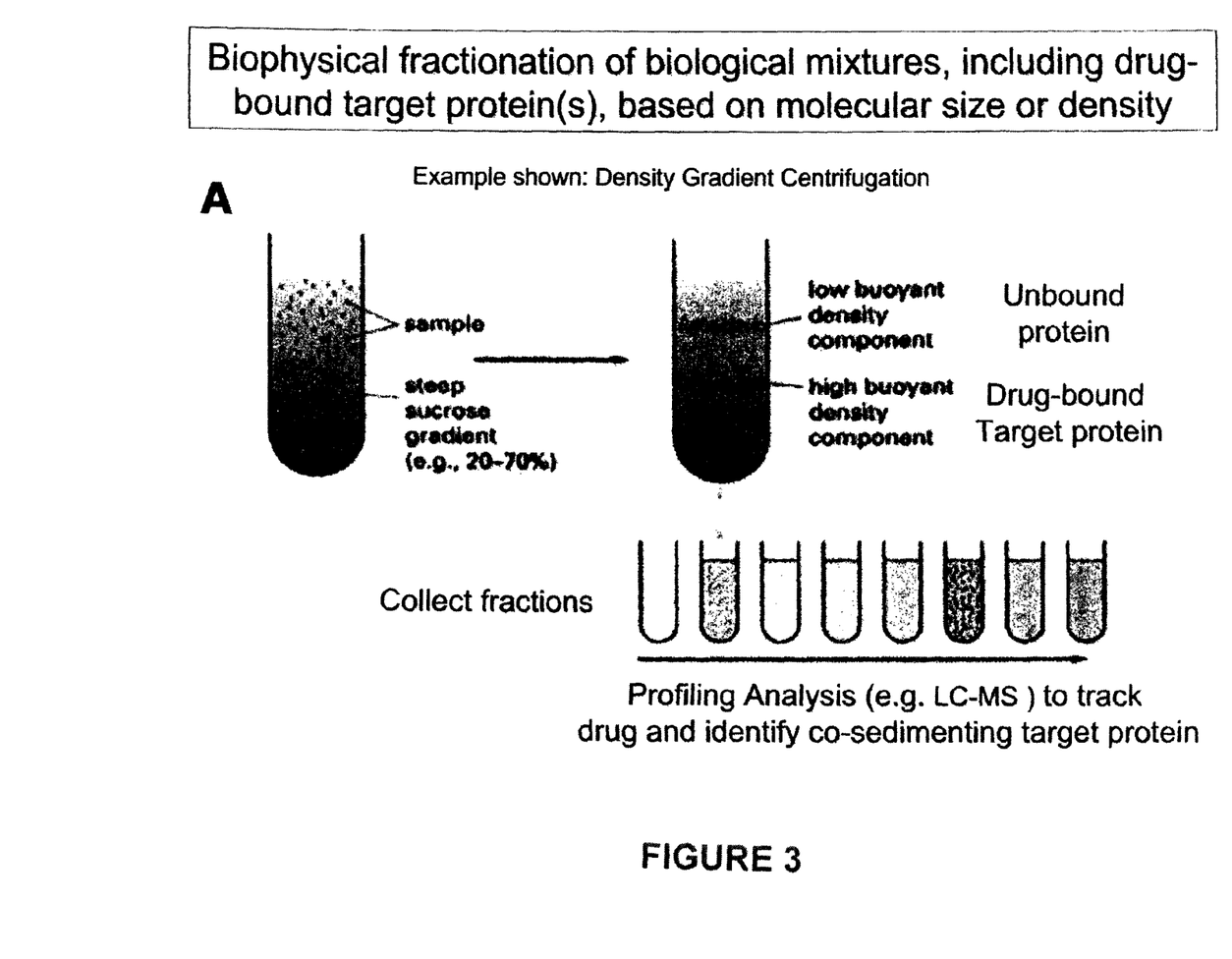
FIG. 3 is a schematic representation of a biophysical fractionation of biological mixtures, including drug-bound target protein(s), based on molecular size or density.

FIG. 3 exemplifies the fractionation of biological mixtures, including drug-bound target protein(s), based on molecular size or density. The recovered fractions may be analyzed by liquid chromatography-mass spectrometry (LC-MS) to track the drug and identify co-sedimenting target(s).

Example 2

Figure 4:
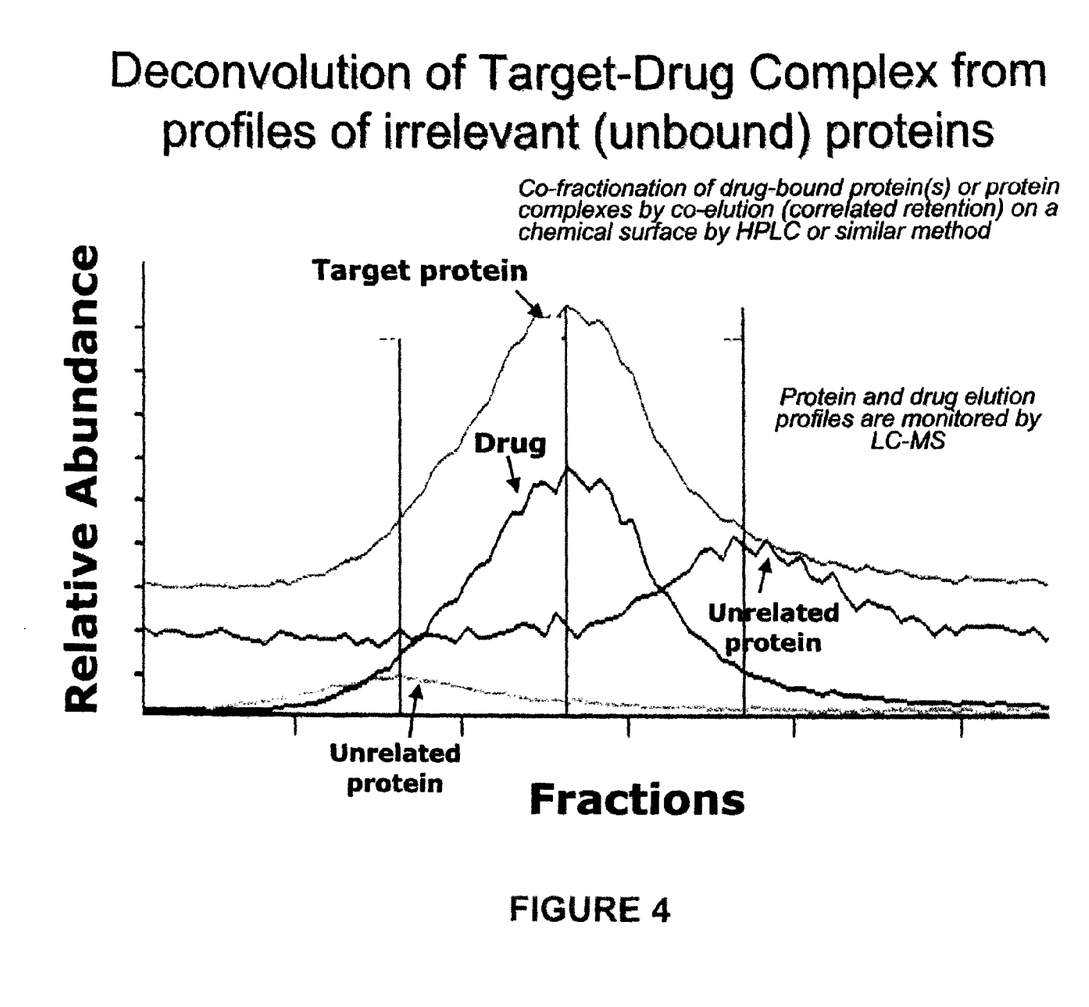
FIG. 4 is an elution profile of proteins and drug-proteins complex as monitored by LC-MS.

An example of de-convolution of target-drug complex from profiles of unbound proteins is shown in FIG. 4. The elution profile is followed by LC-MS and demonstrates the co-elution of target and drug.

Example 3

Figure 5:
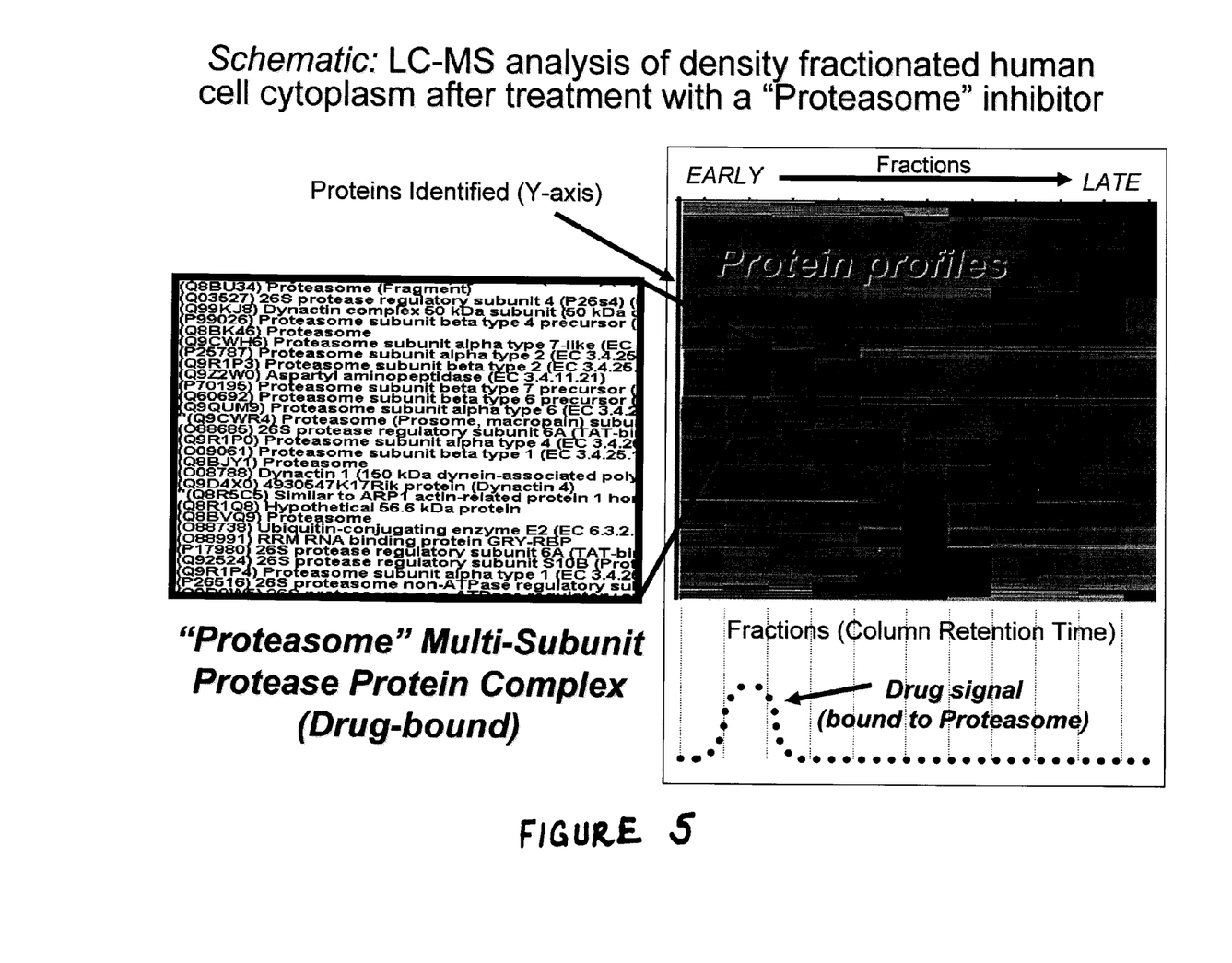
FIG. 5 is a LC-MS analysis of density fractionated human cell cytoplasm after treatment with a "Proteasome" inhibitor.

As mentioned above, chemical compounds may bind to protein complexes (proteasomes). FIG. 5 provides an example in which an LC-MS analysis of a density fractionated human cell cytoplasm after treatment with a proteasome inhibitor reveals the identity of the proteasome bound by the drug.

Example 4

Figure 6A:
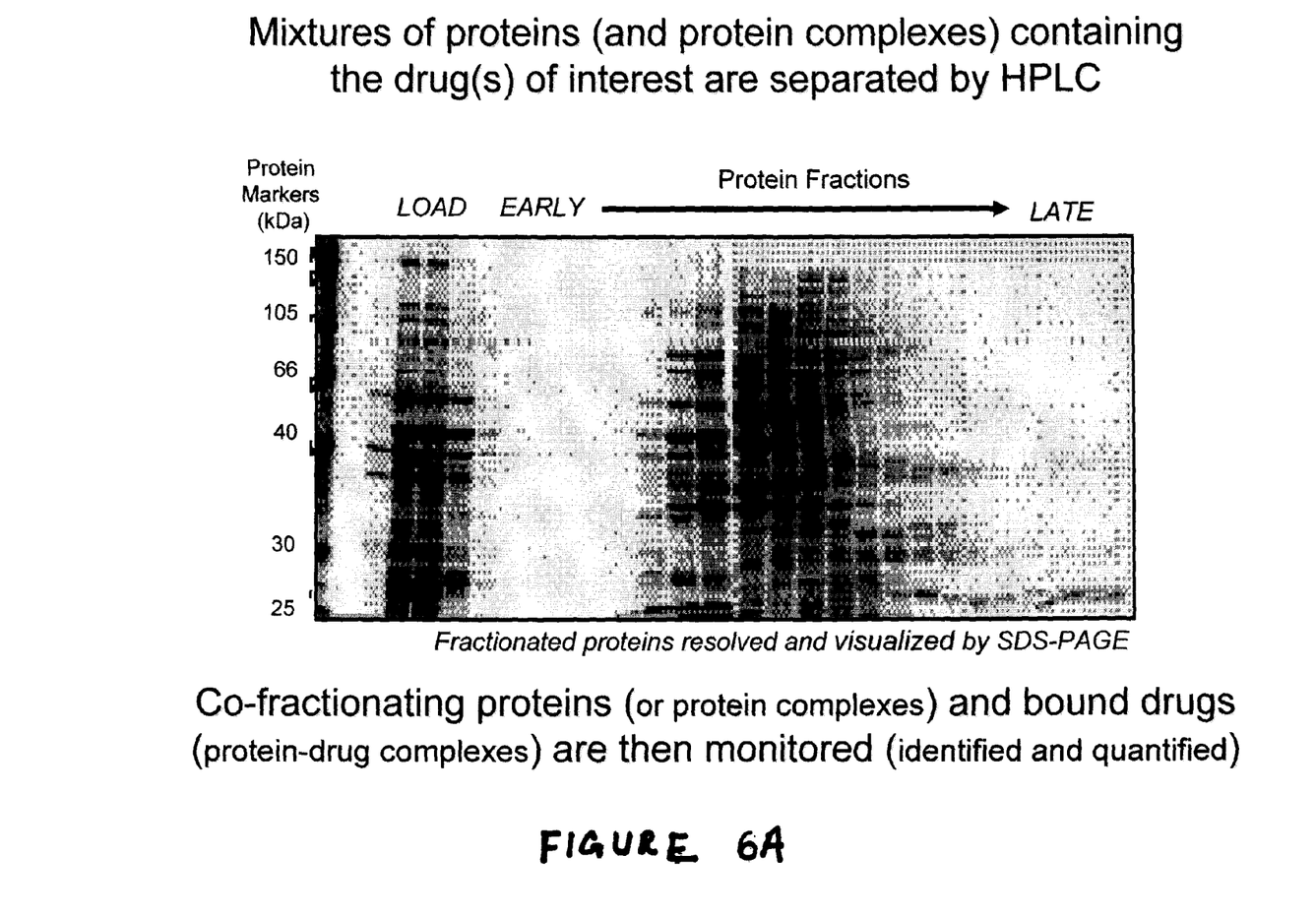
FIG. 6A is am SDS-PAGE of HPLC separated proteins that have been incubated with a drug.
Figure 6B:
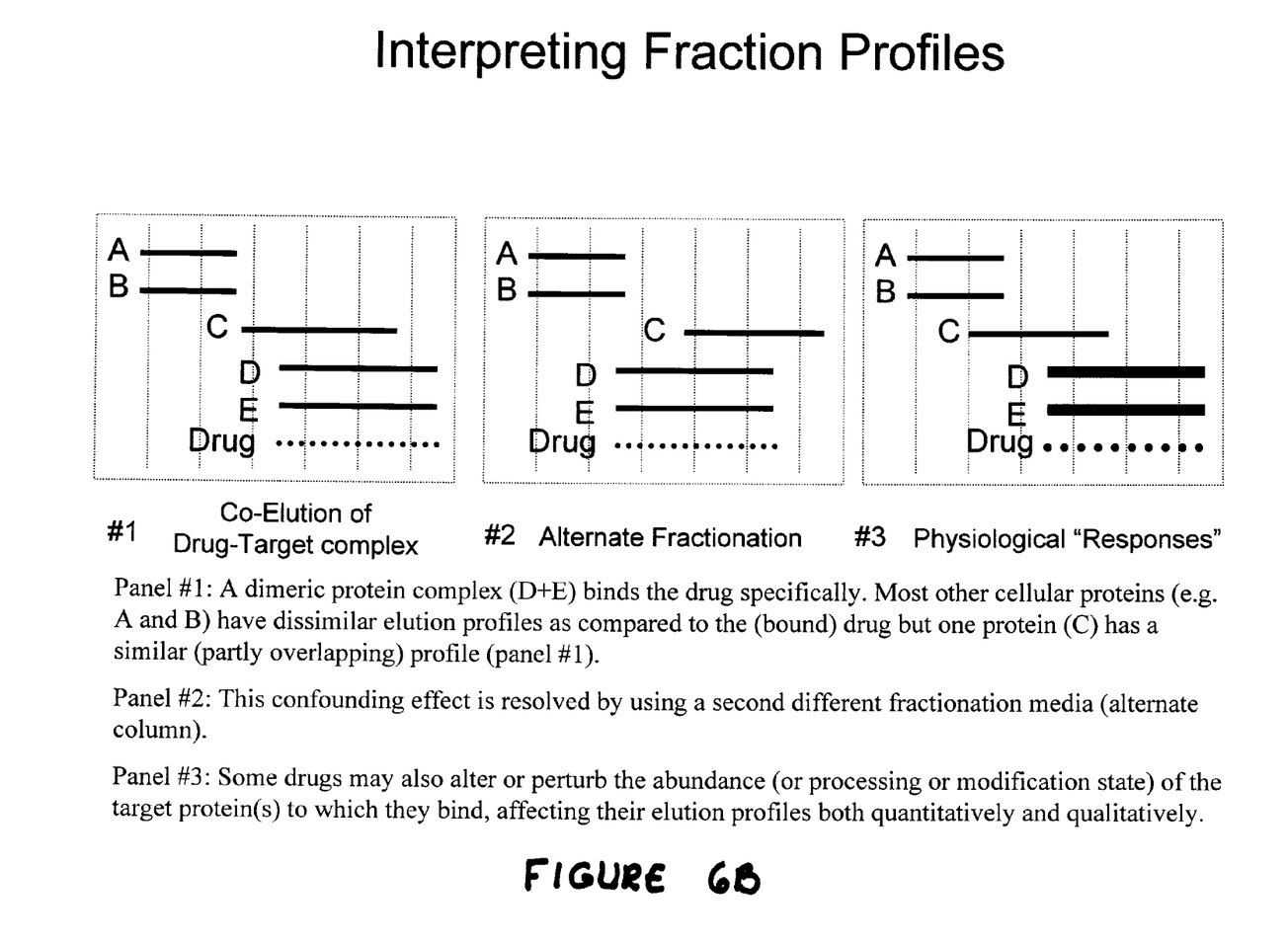
FIG. 6B is schematic representation of protein fractions profiles.

FIG. 6 exemplifies how different separation conditions may resolve partially overlapping fractions. FIG. 6A shows an SDS-PAGE analysis of resolved proteins. In panel #1 of FIG. 6B a dimeric protein complex (D+E) is shown to bind the drug specifically. Most other cellular proteins (e.g. A and B) have dissimilar elution profiles as compared to the (bound) drug but one protein (C) has a similar (partly overlapping) profile. This confounding effect is resolved by using a second different fractionation media (alternate column) as shown in panel #2.

The figure also illustrates how the method of the invention may be used to monitor the effect of a chemical on protein expression which provides information on the pharmacological profile. Thus some drugs may alter or perturb the abundance (or processing or modification state) of the target protein(s) to which they bind, affecting their elution profiles both quantitatively and qualitatively as shown in panel #3.

Example 5

Figure 7:
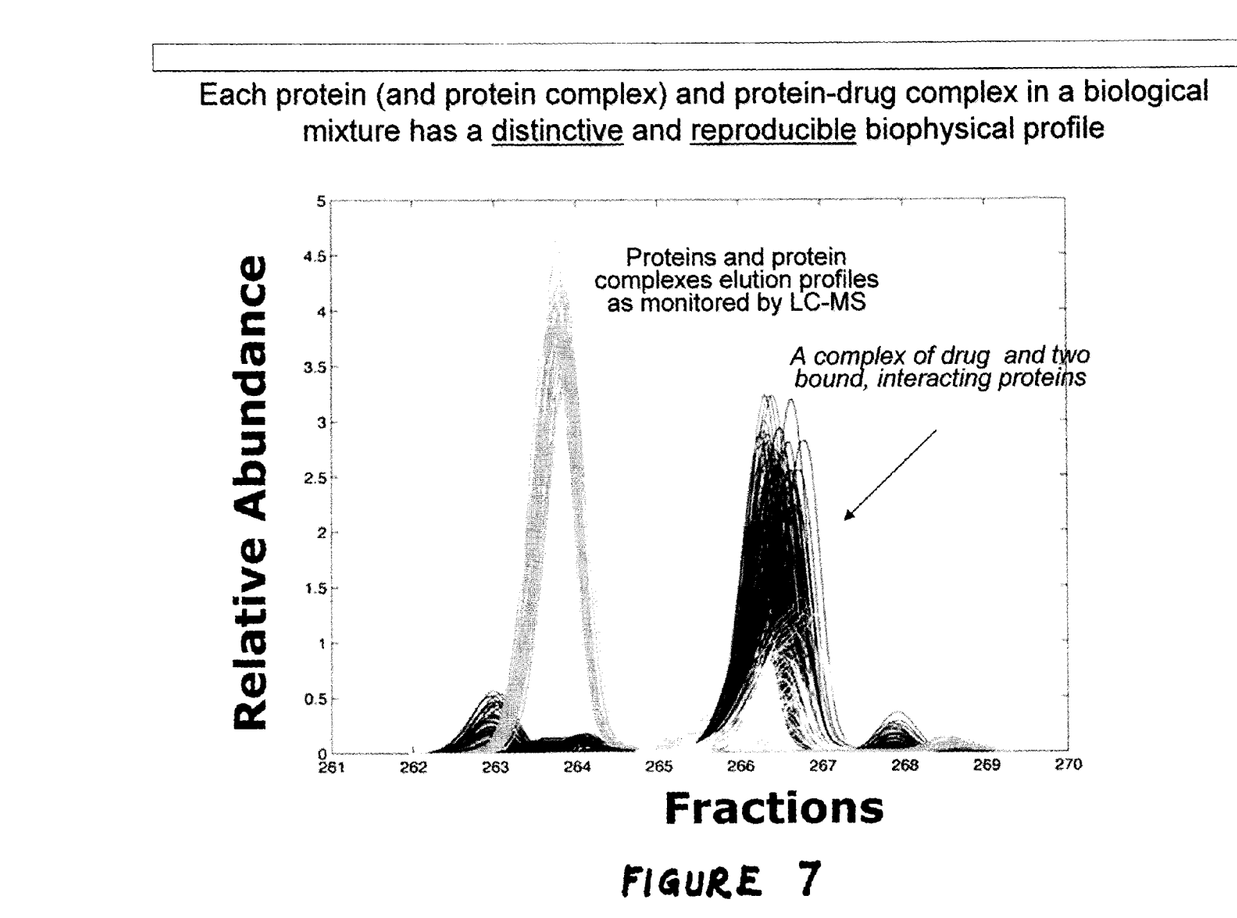
FIG. 7 is an elution profile of proteins and protein complexes as monitored by LC-MS.

The example provided in FIG. 7 indicates the reproducibility of the method by showing that proteins and analyte-proteins complex in a biological mixture has a distinctive and reproducible biophysical profile.

Example 6

Using the method of the present invention, the selective targeting of by the anti-folate compound methotrexate (MTX) is demonstrated. Importantly, DHFR is frequently expressed at elevated levels in many human cancers, while MTX and related anti-folates are frequently used as first line anti-cancer agents.

Figure 8:
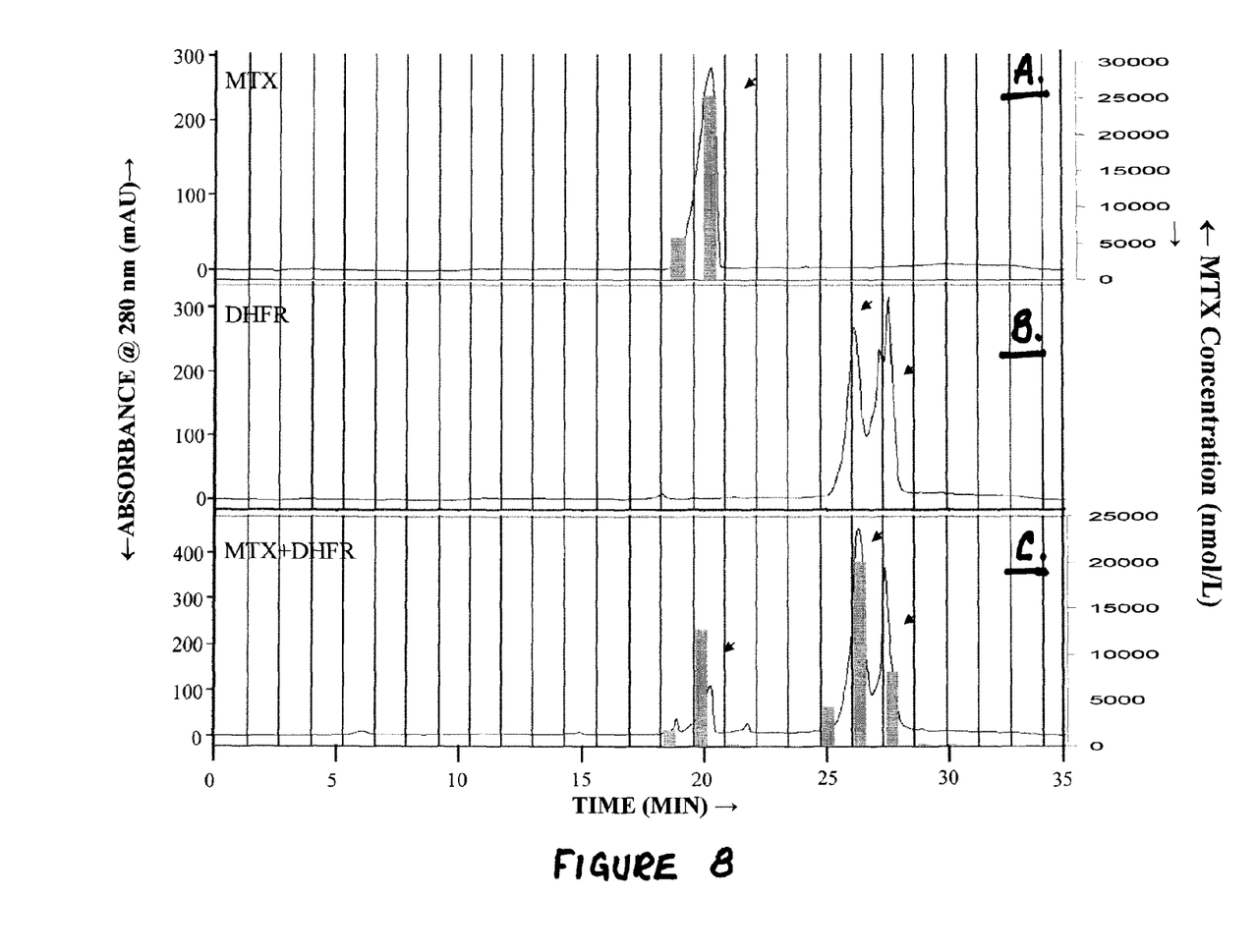
FIG. 8A is an elution profile of Methotrexate (MTX)
FIG. 8B is an elution profile of Dihydrofolate reductase (DHFR)
FIG. 8C is an elution profile of MTX that has been incubated with DHFR.

As reference negative and positive controls, respectively, purified recombinant human DHFR and analytical-grade MTX were either separately or jointly mixed and applied to an ion exchange chromatography support column and subsequently fractionated using a salt buffer gradient using a high-performance liquid chromatography (HPLC) system. Timed fractions of the eluant were collected. The elution characteristics of target protein and the presence of drug were monitored by UV-absorbtion as well as by MS. The corresponding UV-traces are provided in FIG. 8. Quantitation of the amount of drug present in each fraction was measured by Multiple-Reaction Monitoring (MRM), a focused MS scanning procedure commonly used for tracking ionized molecules of interest based on a diagnostic fragment daughter ion species that is characteristically generated after energetic fragmentation, using an external standard for calibration. The identity of the corresponding protein was confirmed by tandem mass spectrometry (MS/MS).

Methods:

Materials

Ultra-pure tris(hydroxymethyl)aminomethane (TRIS base), sodium chloride (NaCl), trichloroacetic acid (TCA), sodium azide ($NaN_3$), ammonium bicarbonate ($NH_4HCO_3$), calcium chloride ($CaCl_2$), high-performance liquid chromatography (HPLC) grade water, HPLC grade acetonitrile (ACN), and HPLC grade glacial acetic acetic (M) were purchased from Fischer Scientific (Whitby, ON, Canada). Hydrochloric acid (6N HCl) was obtained from VWR International (Mississauga, ON, Canada), heptafluorobutyric acid (HFBA) from BioLynx (Brockville, ON, Canada), HPLC grade acetone and tissue culture media from Sigma-Aldrich (Oakville, ON, Canada), and protease cocktail inhibitor from Roche Diagnostics (Laval, QC, Canada). An equal mixture of Poroshell bulk immobilized trypsin (Applied Biosystems; Streetsville, ON, Canada) and TPCK-treated trypsin beads (Pierce Biotechnology; Rockford, Ill., USA) were used for the tryptic digests. A crude soluble total protein cell lysate was prepared by sonication of harvested culture of E. coli grown in rich LB media using in aqueous lysis buffer (20 mM NaCl, 50 mM Tris-HCl pH7.6, 5 mM MgCl, 1 mM Dithiothreitol (DTT), and 1 mM Phenylmethylsulfonylfluoride). The extract was stored at −80° C. prior to analysis.

A 100 ul aliquot of frozen extract was thawed and briefly clarified by centrifugation at 14000 rpm for 10 min in a pre-cooled Eppendorf centrifuge immediately prior to fractionation.

HPLC Sample Fractionation

An integrated Agilent™ 1100 HPLC chromatograph system (Agilent Technologies, Mississauga, ON, Canada) consisting of a vacuum degasser, binary pump, refrigerated autosampler with 100-μl injector loop, thermostatted two column compartment, autocollection fraction module and multi-wavelength detector, was used in this study. Chromatogram acquisition and processing were performed according to basic procedures using the ChemStation™ software. The dual-column set-up, comprising a tandem WAX-CAT (Poly-WAX LPT™, 200×2.1 mm i.d, 5 μm, 1000 Å; PolyCAT AT™, 50×2.1 mm i.d, 5 μm, 1000 Å) two-stage set-up. The system was protected from clogging with a weak anion exchange pre-column guard cartridge. All columns and guards were obtained from Canadian Life Science (Peterborough, ON, Canada). The column compartment was cooled to 17° C. while the other bays were chilled to 4° C. to minimize sample degradation.

Mobile phase Buffer A was prepared by dissolving 1.8 g of Tris in 1 L of 10 mM HCl solution (pH 7.8 obtained without adjustment). Buffer B was prepared by dissolving 35 g of NaCl in Buffer A solution. A small amount (final concentration of 3 mM) of $NaN_3$ was added to minimize microbial outgrowth to each solution, which were also filtered using a 0.22-μm disposable membrane cartridge (Millipore, Cambridge, Canada) before use. Prior to sample injection into the HPLC system, the extracts were briefly clarified by centrifugation and stored in a pre-cooled autoloader. Injections were typically ~120 μg total protein loaded per run. Elution was achieved using multi-step gradient, consisting of six transitions with increasing proportions of buffer B: (step 1; equilibration) 0% B, 0-8 min; (step 2; salt gradient) 0-45% B, 8-38 min; (step 3; high salt rinse) 45-100% B, 38-58 min; (step 4; high salt wash) 100% B, 58-66 min; (step 5; restoration) 100-0% B, 66-68 min; and, lastly, 0% B (step 6; re-equilibration) from 68 to 76 min. The column mobile phase flow rate was fixed at 250 $\mu l.min^{-1}$. The chromatograms were monitored at 280 nm and timed fractions collected using an automated fraction collector cooled to 4° C. A total of 26 fractions were collected per run, with one fraction isolated per ~2.9 min (each ~0.7 ml in volume for two successive injections).

Tandem Mass Spectrometry

Methotraxate levels were monitored using an industry standard MRM procedure. First, 1 part of each fraction was mixed with 4 parts acetonitrile (0.1 mL sample and 0.4 mL acetonitrile) to denature the proteins and release the MTX. The sample was then briefly centrifuged; 0.45 mL of the supernatant was then drawn and evaporated to complete dryness. The pellet was re-dissolved in 0.025 mL of mobile phase buffer and injected into an MDS/Sciex™ API3000 triple quadrupole tandem MS instrument. The basic MRM procedure using a distinctive diagnostic transition was used for detection. The integrated ion signal intensities were normalized relative to a standard calibration curve.

For the proteomic detection, we used single-dimension reverse-phase chromatography coupled online to ion trap tandem MS using standard conditions typically applied to samples of moderate complexity. The protein content of each HPLC fraction was precipitated by adding ice-cold neat TCA solution to a 10% (v/v) final concentration. Following overnight incubation at 4° C., the samples were centrifuged at 14000 rpm for 30 min in a cooled Eppendorf centrifuge. The supernatant was carefully aspirated and 600 μl ice-cold HPLC grade acetone gently added and removed to pH neutralize the protein pellets. The samples were air-dried in the fume-hood for 10 min, and resuspended in digest solution (50 mM $NH_4HCO_3$-1 mM $CaCl_2$) containing a 1:1 slurry of immobilized trypsin beads in a final volume of 60 μl. After incubation for two days at 30° C. with rotation, a 20 μl aliquot was withdrawn, mixed with an equal volume of LC-MS equilibration buffer (5% ACN, 0.5% AA, and 0.02% HFBA in HPLC grade water). The digested peptide mixtures were chromatographically resolved on a 150 μm inner diameter fused silica capillary micro-column (Polymicro Technologies, Phoenix, Ariz., USA) bearing a fine nozzle created with a laser puller (P-2000, Sutter Instruments; Novato, Calif., USA) that was connected in-line to an LTQ linear ion trap tandem mass spectrometer (Thermo Finnigan; San Jose, Calif., USA). The columns were pre-packed with ~8 cm of 5 μm Zorbax 300SB $C_{18}$ resin (Agilent Technologies; Mississauga, ON, Canada) and were interfaced to a custom electrospray ion source. A Surveyor quaternary HPLC pump (Thermo Finnigan) was used to deliver a stable tip flow rate of ~0.250 $\mu l.min^{-1}$ during the peptide separations. Elution of the peptides was achieved using a 90 min gradient (0 to 30% ACN in 60 min, then 30 to 80% ACN over 15 min, and returning to 0% buffer B in 15 min). Data-driven precursor ion selection and fragmentation was achieved in a fully automated data-dependent manner with dynamic target exclusion setting enabled.

The SEQUEST database search algorithm was used to match up all the acquired spectra to peptide sequences encoded in a protein database downloaded from the European Bioinformatics Institute. A probabilistic model was used to evaluate and assign confidence scores to all putative matches. Proteins were considered positively identified if detected with two or more high confidence (p-value <0.10) peptide candidates, each passing a minimum likelihood threshold corresponding to a 90% or greater probability of being correct.

Results

As can be seen in panel A, FIG. 8, free MTX alone was retained by the column, eluting principally in fractions 19-20. Conversely, as seen in FIG. 8 B, the DHFR protein bound somewhat more strongly, emerging as two peaks that were collected in fractions 26-27 and 27-28, respectively; these represent closely related isoform variants of DHFR as each was identified by MS/MS. Conversely, in the presence of its protein target, FIG. 8C, the retention of MTX was markedly and quantitatively shifted such that it now perfectly co-eluted with DHFR, as would be expected due to the tight physical interaction of the drug to its cognate receptor protein. These data indicate that drug-target binding is preserved during the HPLC fractionation procedure and that the interaction and co-fractionation of the drug with its cognate protein target can be revealed by monitoring and comparing the respective elution profiles of the ligand and its target alone or together.

As a more stringent test for evaluating the specificity and the capability of the co-fractionation principle to allow for the discernment of a selective interaction of a compound or drug with a single unique target protein present amongst many other irrelevant competitor proteins, the same series of fractionation experiments were re-performed, except now spiking in the drug and/or the recombinant DHFR target into a complex background mixture consisting of soluble proteins extracted from a crude whole cell lysate prepared from the bacterium *E. coli*.

Figure 9:
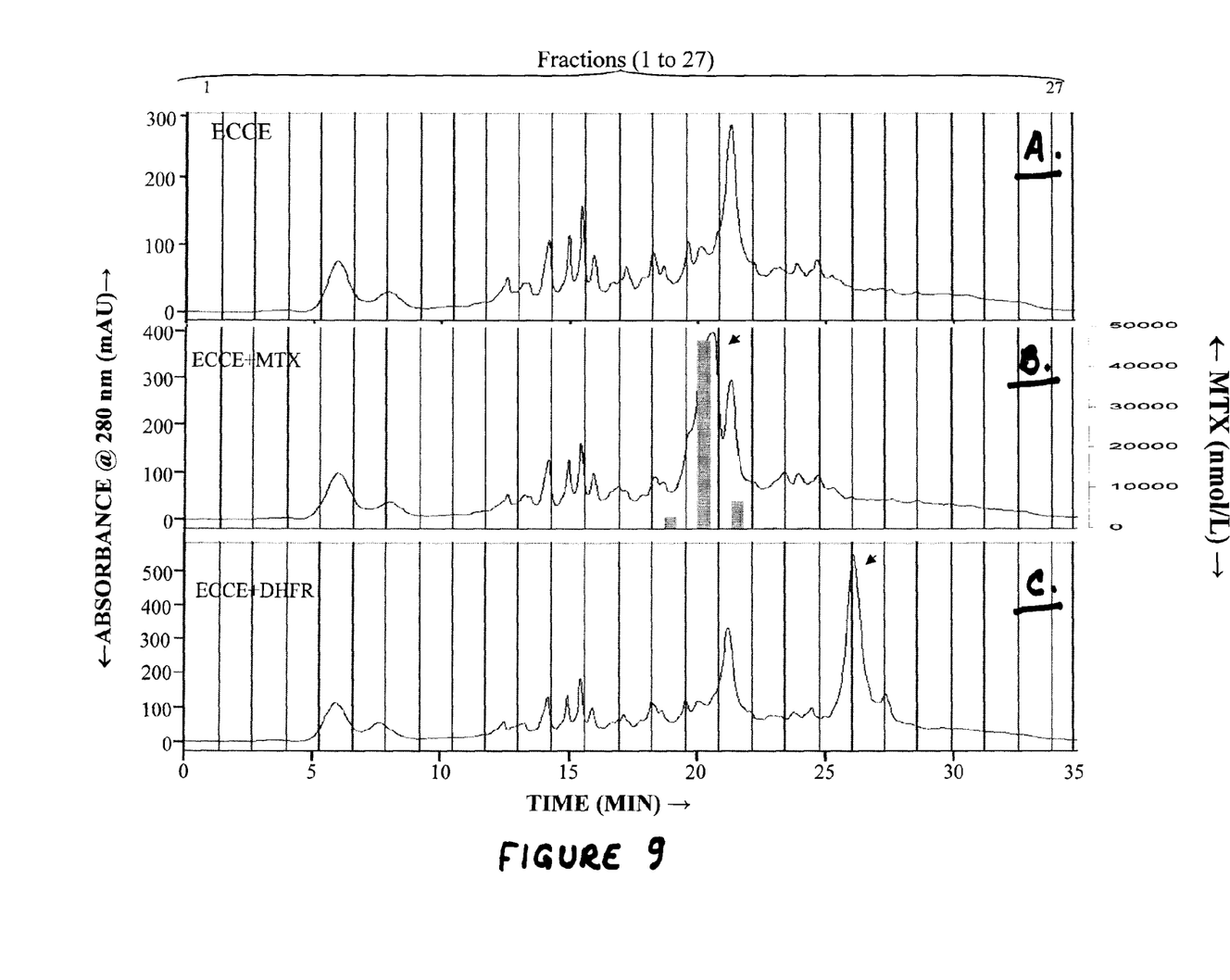
FIG. 9A is an elution profile of an *E. coli* cellular extract (ECCE)
FIG. 9B is an elution profile of ECCE incubated with MTX.
FIG. 9C is an elution profile of ECCE spiked with DHFR.
FIG. 9D is an elution profile of a mixture of ECCE, MTX and DHFR.
FIG. 9E is an elution profile of an *E. coli* cellular extract (ECCE) as also shown in FIG. 9A.

The data provided in FIG. 9 show the UV-traces and corresponding quantified MS signal recorded after ion-exchange HPLC-based fractionation of either the cell lysate alone (FIG. 9A), MTX-spiked extract only (FIG. 9B), DHFR-spiked extract only (FIG. 9C), or the cell lysate spiked with both MTX and DHFR (FIG. 9D). Comparison of the traces again revealed the tight nearly stoichiometric co-elution of the bulk of the drug with its target protein, despite the presence of an excess on non-specific competitor proteins, while no non-specific binding of the drug to any *E. coli* proteins was detected. Hence, the correlated co-elution of the drug with its protein target indicates a specific and tight physical interaction. These data are consistent with the known biophysical properties previously reported for the interaction of DHFR with MTX.

While the invention has been described in connection with specific embodiments thereof, it will be understood that it is capable of further modifications and this application is intended to cover any variations, uses, or adaptations of the invention following, in general, the principles of the invention and including such departures from the present disclosures as come within known or customary practice within the art to which the invention pertains and as may be applied to the essential features herein before set forth, and as follows in the scope of the appended claims.

The invention claimed is:

1. A method for determining the identity of an unknown protein target of an analyte said method comprising:
   a) contacting said analyte with a sample comprising a plurality of macromolecules so as to allow binding of said analyte to the unknown protein target thereby generating an analyte-target complex wherein the analyte and protein target are underivatized and free in solution;
   b) next resolving said macromolecules including said analyte-target complex liquid chromatography to produce macromolecule fractions, wherein binding of said analyte to said protein target is maintained during said resolving and said resolving takes place under non-denaturing conditions;
   c) analyzing a plurality of the macromolecule fractions including at least one macromolecule fraction containing the analyte-target complex to identify fractions that contain the analyte;
   d) analyzing at least one macromolecule fraction that contains the analyte with mass spectrometry to determine the mass spectrum and the identity of the protein target, wherein the macromolecule fraction that contains the analyte is subject to proteolytic degradation prior to analyzing the macromolecule fraction with mass spectrometry.

2. The method of claim 1, wherein step d) comprises analyzing a plurality of macromolecule fractions containing the analyte with mass spectrometry to obtain a plurality of mass spectra of the analyte-protein target.

3. The method of claim 1, wherein the analyzing step comprises determining the identity of the protein target by comparing the mass spectrum of the macromolecule fraction that contains the analyte to the mass spectra of a protein mass spectrum database including the protein target.

4. The method of claim 1, wherein the analyte comprises a drug or a drug metabolite.

5. The method of claim 1 wherein said resolving is performed using two or more separation protocols, each protocol exploiting a different physico-chemical property of said macromolecules, and wherein each fraction identified as comprising said analyte is analyzed to identify said one or more protein target and wherein said identified macromolecule targets are compared to validate a protein target identity.

6. The method as claimed in claim 1 wherein said protein target is a protein complex and wherein said protein complex is maintained during said resolving.

7. The method of claim 5 wherein said two or more separation protocols are selected from the group consisting of chromatography, centrifugation, and electrophoresis.

8. The method as claimed in claim 7 wherein said step of separating comprises obtaining a cellular extract or sub-fraction.

9. The method as claimed in claim 8 wherein said cellular extract is selected from whole cell extract, membrane extract and an organelle extract.

10. The method as claimed in claim 9 wherein said organelle is selected from nucleus, mitochondria, membranes, Golgi apparatus, vacuole, and chloroplast.

11. The method of claim 1 wherein said step of contacting comprises incubating said analyte with cells.

12. The method of claim 1 wherein said step of contacting comprises incubating said analyte with cell extracts.

13. The method of claim 1 wherein a plurality of analytes is simultaneously contacted with said sample.

14. The method of claim 1, wherein the step c) and/or step d) comprises comparing an elution profile of the target with an elution profile of the analyte-target complex and identifying quantitative or qualitative alterations in the elution profile of the target.

15. The method of claim 1, wherein the step d) comprises collision induced dissociation or ion fragmentation mass spectrometry of the protein target leading to fragmentation of intense precursor protein ions in the mass spectrum to provide amino acid sequence of the protein.

16. The method of claim 1, wherein the resolving step comprises 1D and 2D-LC separations and step d) comprises LC-MS/MS.

17. The method of claim 1, wherein step c) comprises analyzing the plurality of the macromolecule fractions using mass spectroscopy.

18. The method of claim 17, wherein step c) and step d) are performed simultaneously.

* * * * *

UNITED STATES PATENT AND TRADEMARK OFFICE
CERTIFICATE OF CORRECTION

PATENT NO.         : 8,192,999 B2                                          Page 1 of 1
APPLICATION NO.    : 11/813331
DATED              : June 5, 2012
INVENTOR(S)        : Andrew Emili It is certified that error appears in the above-identified patent and that said Letters Patent is hereby corrected as shown below:

1. In claim 1, part b) at column 13, line 47, "analyte-target complex liquid" should read -- "analyte-target using complex liquid" --; and 2. In claim 2 at column 14, line 7, "mass spectra of the analyte protein target" should read -- "mass spectra of the protein target". --

Signed and Sealed this
Eleventh Day of September, 2012

David J. Kappos
*Director of the United States Patent and Trademark Office*